(12) United States Patent
Dieβel et al.

(10) Patent No.: US 9,128,072 B2
(45) Date of Patent: Sep. 8, 2015

(54) APPARATUS FOR AUTOMATICALLY PERFORMING ANALYSES

(75) Inventors: Edgar Dieβel, Köln (DE); Ingmar Dorn, Köln (DE); Michael Habig, Kiel (DE); Mike Küster, Düsseldorf (DE); Klaus Ochmann, Leverkusen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 1091 days.

(21) Appl. No.: 13/121,581

(22) PCT Filed: Sep. 24, 2009

(86) PCT No.: PCT/EP2009/006891
§ 371 (c)(1),
(2), (4) Date: Jun. 13, 2011

(87) PCT Pub. No.: WO2010/037497
PCT Pub. Date: Apr. 8, 2010

(65) Prior Publication Data
US 2011/0269239 A1    Nov. 3, 2011

(30) Foreign Application Priority Data
Oct. 1, 2008   (EP) .................................... 08017274

(51) Int. Cl.
G01N 35/02     (2006.01)
G01N 35/00     (2006.01)
G01N 35/10     (2006.01)

(52) U.S. Cl.
CPC .... G01N 35/028 (2013.01); *G01N 2035/00306* (2013.01); *G01N 2035/00326* (2013.01); *G01N 2035/1051* (2013.01); *Y10T 436/11* (2015.01)

(58) Field of Classification Search
CPC .......... G01N 35/0092; G01N 35/0099; G01N 1/312; G01N 35/00029; G01N 35/10; G01N 2035/00752; G01N 35/04; G01N 2035/00089; G01N 35/028; G01N 2035/306; G01N 2035/326; G01N 2035/1051; Y10T 436/11
USPC ................................................ 436/43; 422/63
See application file for complete search history.

(56) References Cited

U.S. PATENT DOCUMENTS 5,592,289 A * 1/1997 Norris ............................ 356/244
5,702,950 A * 12/1997 Tajima ............................ 436/49

(Continued)

FOREIGN PATENT DOCUMENTS

DE   4210963 A1   10/1993
EP   0353591 B1   2/1990

(Continued)

OTHER PUBLICATIONS

International Search Report dated Jan. 28, 2010.

*Primary Examiner* — Lyle Alexander
*Assistant Examiner* — Dwan A Gerido
(74) *Attorney, Agent, or Firm* — Norris McLaughlin & Marcus, P.A.

(57) ABSTRACT

The present invention relates to an apparatus and a method for automatically performing chemical, biochemical and biological analyses using the apparatus. The apparatus comprises: a plurality of subsystems for each performing different operations on microtiter plates; a transporting subsystem for automated movement of microtiter plates in three directions X, Y and Z in order to transport plates from one subsystem to another subsystem within the apparatus; a liquid handler comprising at least two liquid handling probes, wherein said liquid handler is integrated in the transporting subsystem; an insertion/removal subsystem for inserting, removing and storing microtiter plates and equipment for sampling and dilution operations, wherein said insertion/removal subsystem is mechanically operated, without the need for electrical components implemented in that subsystem.

20 Claims, 14 Drawing Sheets

(56) References Cited

U.S. PATENT DOCUMENTS

| | | |
|---|---|---|
| 6,267,927 B1 | 7/2001 | Pomar Longedo et al. |
| 2003/0049170 A1 | 3/2003 | Tamura et al. |
| 2005/0079106 A1* | 4/2005 | Baker et al. .................. 422/100 |
| 2005/0124013 A1 | 6/2005 | Bonne et al. |
| 2005/0220675 A1* | 10/2005 | Reed et al. .................. 422/100 |
| 2006/0110287 A1 | 5/2006 | Kraemer et al. |
| 2010/0267771 A1 | 10/2010 | Bott et al. |

FOREIGN PATENT DOCUMENTS

| | | |
|---|---|---|
| EP | 0918221 A1 | 5/1999 |
| EP | 1293781 B1 | 3/2003 |
| EP | 1710587 A | 10/2006 |
| WO | 0008472 A | 2/2000 |
| WO | 2004059288 A | 7/2004 |
| WO | 2005047858 A | 5/2005 |
| WO | 2006094388 A1 | 9/2006 |

* cited by examiner

APPARATUS FOR AUTOMATICALLY PERFORMING ANALYSES

CROSS-REFERENCE TO RELATED PATENT APPLICATIONS

This is an application filed under 35 USC §371 of PCT/EP2009/006891 filed on Sep. 24, 2009 claiming priority to EP 08017274.5 filed on Oct. 1, 2008.

BACKGROUND OF THE INVENTION (1) Field of the Invention

The present invention relates to an apparatus and a method for automatically performing chemical, biochemical and biological analyses.

(2) Description of Related Art

Automated analyzers are well known in the prior art and are used for example by diagnostic laboratories for the rapid and reliable detection of analytes in a variety of biological samples. Analyzers are routinely used to perform a wide variety of assays, most of which involve immunoassays which exploit the high affinity and selectivity of an antibody for its antigen.

Analyzers with very high throughput capabilities are usually modular in form, with each separate module performing a single step of the assay. For example, modules commonly exist for fluid liquid handling, incubating, vortexing, transporting and reading and analyzing the assay result. These modules are then robotically interconnected to provide full automation.

Although microtitre plate liquid handling systems and single function microtitre plate systems such as washers, incubators, agitators and readers are well known in the prior art, only a few examples of compact fully automated microplate analyzers have been disclosed.

One example of such an integrated analyzer is described in WO 2006/094388 A1 This analyzer comprises fully integrated subsystems for liquid handling and optical reading and allows the transport of microtitre plates and the parallel detection of several analytes in one microtitre plate using different photometric characteristics. A plurality of discrete carrier trays is used for holding and transporting microtitre plates and other assay consumables.

EP 0 918 221 B1 discloses an apparatus for performing automatic tests on samples for ELISA (Enzyme-linked Immunosorbent Assay) tests, which is constituted by two functionally separate regions of which the first, which permits interactive access by the user, permits loading of the samples, controls, calibrations, diluents and equipment necessary for performing the sampling and the dilutions. The apparatus then performs the operations relating to the sampling and dilutions of the samples and transports the plate to the second region in which the rest of the operations are performed, the first region being left free for the loading of further series. The device is further characterized by a series of containers for the storage of the auxiliary liquids for the process and for the collection of washings and waste.

EP 1 293 781 B1 discloses an automatic analyzing apparatus for detecting object substances in specimens such as for immunity analyses utilizing the reaction between antigen and antibody and chemicobiological analyses. The automatic analyzing apparatus comprises a reaction portion for causing a specimen substance to act on a reagent commensurate therewith in a reaction vessel, a detecting portion for detecting signals derived from the reagent and a cleaning portion for removing the specimen substance or unreacted reagent or cleaning reaction liquid after the reaction is complete. These reaction, detection and cleaning portions are arranged on turntables.

EP 0 353 591 B1 discloses a semi-automated biological sample analyzer for performing enzyme immunoassays for human IgE class antibodies specific for a panel of preselected allergens in each of a plurality of biological samples. The analyzer comprises a carousel for positioning and holding a plurality of reaction cartridges. Each reaction cartridge includes a plurality of isolated test sites formed in a two-dimensional array in a solid phase binding layer contained within a reaction well which is adapted to contain a biological sample to be assayed.

The region for the input of samples and equipment necessary for performing sampling and dilutions can be subject to contamination and liquid spillover. One disadvantage of prior art analyzers is that there is often an electrically driven drawer for containing the samples and equipment necessary for performing the sampling and dilutions. An electrically driven drawer is easily decomposed by contaminations. Therefore there is a need to have means of inserting samples whose functionality is not affected by contaminations or liquid spillover.

Analyzers can also be subject to operational errors despite automatic operation and minimum human intervention. Since the samples and equipment necessary for sampling can be very costly, especially in the case of biochemical and or biological clinical tests, there is a need to recognize operational errors to avoid waste of costly substances. The mechanisms for recognizing operational errors must also be inexpensive and uncomplicated, in order to avoid increasing the complexity of the fully integrated and therefore already complex analyzer.

In order to achieve high flexibility, it is necessary to integrate as much functionality as possible in an analyzer. Hence, solutions for increasing functionality without increasing complexity, cost and/or sensitivity are required.

BRIEF SUMMARY OF THE INVENTION

One object of the present invention is therefore to provide an apparatus for automatically performing analyses which is flexible and applicable for a wide variety of analyses.

Another object of the present invention is to provide an automatic analyzer in which human intervention is reduced to a minimum and operational errors are avoided.

Another object of the present invention is to provide an automatic analyzer which comprises effective mechanisms for detecting operational errors with a minimum of additional means.

Another object of the present invention is to provide an automatic analyzer which is robust and not sensitive to contamination and liquid spillover.

Another object of the present invention is to provide a highly integrated analyzer of low complexity.

Surprisingly, it has now been found that the above objects are achieved by an apparatus according to claim 1.

The present invention therefore relates to an apparatus for automatically performing chemical, biochemical or biological analyses in microtitre plate format, the apparatus comprising at least

- subsystems for performing different operations on microtitre plates such as agitation and thermal incubation and an optical reading system for the detection of optical characteristics such as absorbance, luminescence, fluorescence, fluorescence polarization and time-resolved fluorescence;

means for the automated movement of microtitre plates in three directions X, Y and Z in order to transport plates from one subsystem to another subsystem within the apparatus;

means for liquid handling, wherein said means for liquid handling are integrated in said means for the automated transportation of microtitre plates;

means for inserting, removing and storing microtitre plates and other equipment for sampling and dilution operations, characterized in that said means for inserting, removing and storing microtitre plates is mechanically operated, without the need for electrical components implemented in that subsystem.

The apparatus, hereinafter referred to as the analyzer, comprises a number of subsystems, such as for example liquid handling, agitation and thermal incubation stations as well as an optical detection system.

The automated analyzer performs all steps for detecting analytes on supports having a plurality of cells or wells for facilitating the parallel and orderly processing of samples. Chemical assays for analyte detection are preferably conducted in a microtitre plate-based format. Microtitre plates are available in a number of formats, Commonly used formats are 96-well (8 rows×12 columns), 384-well (16 row×24 columns) and 1536-well (32 rows×48 columns) microtitre plates which are occasionally dividable into individual strips containing one column or row of wells.

The analyzer according to the invention has a transporting unit for transporting microtitre plates and containers and a liquid handling unit. The transporting unit and the liquid handling unit are preferably combined in one unit. By means of the transporting unit, the liquid handling unit can be moved in three directions X, Y and Z inside the analyzer and can therefore be moved towards individual wells in the mictrotitre plates. Z is the direction of the force of gravity and X and Y are the directions along the plane vertical to the Z direction. The liquid handling unit is arranged above the subsystem.

The liquid handling unit comprises at least two movably designed probes for taking up and releasing liquids in order to be able to carry out several liquid handling operations at the same time. The probes extend downwards in the Z direction from an upper movable holder. In a preferred embodiment 4 liquid handling probes are present, the separating space between any two neighbouring probes being adjustable in at least one direction, thus enabling the direct and independent pinpointing of individual wells.

Usually the probes are charged with liquids via syringe pumps. At the tips of said probes, disposable pipette tips from a pipette tip box may be attached by pressing the liquid handling probe into an opening in the pipette tip, thereby establishing a seal between the pipette tip and the liquid handling probe. These disposable tips may be released from the liquid probe by moving the liquid handling probe in the Z direction through openings having a diameter larger than the outer diameter of the liquid handling probe and smaller than the outer diameter of the disposable pipette tip.

In a preferred embodiment plates and containers are moved between the integrated subsystems using removable extensions. These removable extensions can be reversibly fastened to the transporting unit and can hold the microtitre plates and/or containers.

In a preferred embodiment these removable extensions are attached to the liquid handling probes. For this purpose the removable extensions preferably have a conically shaped cavity into which a liquid handling probe can be inserted and clamped into. Clamping forces prevent the probe from slipping out of the cavity. In a preferred embodiment two removable extensions attached to two liquid handling probes are used for bolding and transporting a particular object. For this purpose the removable extension preferably has a flat rough surface. The objects to be transported are clamped between the opposing surfaces of two removable extensions. The roughness of the surface increases the friction between the object and the surface and thus prevents the object from slipping away.

In addition, the removable extensions have means for releasing them from the transporting unit. In a preferred embodiment the removable extensions have at least one additional cavity vertical to the Z direction, into which a protrusion on the analyzer can be introduced. If a removable extension is attached to a protrusion on the analyzer in this manner and the liquid handling probe is moved upwards, the forces between the cavity and the liquid handling probe are overcome and the liquid handling probe slips out of the cavity, whereas the extension remains attached to the protrusion on the analyzer. The removable extensions can for example be made of metal or plastic or a combination thereof.

The reagents for the assay are stored in the microtitre plates and/or additional containers and assay reactions are carried out in the microtitre plates. The apparatus is able to perform all steps of homogeneous or heterogeneous assays such as piercing containers for access, dissolving reagents, diluting samples, controls and standards, followed by incubation at a predefined temperature, agitation and reading using absorbance, turbidimetric, luminescent and fluorescence reading, including the time-resolved mode and polarization mode of fluorescence reading, on microtitre plates. Thus a multitude of different analytes from at least one sample can be detected automatically.

The insertion/removal and storage system of the analyzer of the present invention is characterized by the absence of any electrical components. Analyzers known from the prior art are characterized e.g. by motor-driven opening and closing mechanisms. By contrast, the insertion/removal system of the analyzer according to the invention has at least one drawer which is movable and can he opened and closed in a purely mechanical manner. The insertion/removal system according to the invention has the advantage that it is not affected by splashes or leaks of substances.

The assay consumables, assay reagents and containers can be placed in the drawer, which is located beneath the area of the holder for the liquid handling probes. The drawer is extractable from beneath said liquid handling area to enable easy access thereto by the operator, such as for example for refilling or replacing the consumables and reagents in predefined positions in the drawer.

In a preferred embodiment the base plate of the drawer contains wells that define the positions of containers with different footprints. These wells are characterized, in a preferred embodiment, by a conical opening, thus allowing the easy insertion and exact positioning of the containers. This base plate consists of a chemical-resistant material such as stainless steel or plastic, or it is coated by chemical-resistant materials such as polyether, polyester, polytetrafluoroethylene or the like. In a preferred embodiment the base plate is designed in one piece, consists of a chemical-resistant surface and does not have any exposed projections, thus facilitating cleaning and chemical sterilization.

No tools are required for exchanging the base plate of the drawer, the position of the base plate being fixed by at least two holding means or fasteners (such as clamps, screws, and the like) which, in a preferred embodiment, can be released manually. Base plates with at least two different layouts can be attached to the drawer without any tools being required by the user. Base plates with different layouts can provide differences in functionality, such as those used for performing various detection procedures and those used for the gravimetric calibration of the liquid handling probes. Discrimination of the base plate installed in the drawer is preferably achieved by detecting the pattern of the presence or absence of surfaces in said drawer using protrusions which extend in the Z direction from the holder for the liquid handling probes and are movable in at least one direction. These protrusions perform at least one movement in at least the Z direction to at least one predefined position until their movement is arrested when they come into contact with a surface or when they reach a specific required position. The travel path of the protrusion up to its contact with a surface or on reaching a required position is evaluated and compared to predefined values. In a preferred embodiment the evaluation of the distance covered by a protrusion is determined according to the degree to which the full distance which could possibly he covered by the protrusion is cut short when the protrusion comes into contact with a surface or when it reaches a specific required position. The protrusions also preferably consist of the liquid handling probes. Hereby, the surface contact can be measured by different means as by step losses of stepping motors, electrical impedance, ultrasonic or optical reflection, or by a pressure based system as described in the following. The presence or absence of surfaces can be registered by pressure changes of a gas being pumped through a nozzle onto such surfaces. In a preferred embodiment surfaces are detected by using a liquid handling probe: A gas is intermittently or continuously pumped by a syringe pump through the liquid handling probe. There is a pressure detector installed inside the connections between the syringe pump and the liquid handling probe which detects the pressure, which is required to pump the gas out of the liquid handling probe. When the nozzle of the liquid handling probe approaches a surface the opening of the liquid handling probe is made smaller or completely blocked when the liquid handling probe touches the surface. A higher pressure is needed to pump the gas out of the liquid handling probe, the higher pressure being measured by the pressure detector. Alternatively to the issuing of gas through the nozzle the gas can also be aspirated through the nozzle. This detection scheme is known to be used for the detection of liquid surfaces to determine the respective filling degree of a vial or container. Surprisingly it has been found, that it can be also applied to the detection of solid surfaces and therefore for the detection of the presence or absence of certain elements within/of the analyzer. Various base plates can have protrusions in various positions, the presence of which can be checked in a preferred embodiment by the liquid handling probe which is moved by means of the transporting unit to the corresponding surface of a protrusion.

The drawer is characterized by having at least one base plate at one level in the Z-direction. In a preferred embodiment the drawer has at least two plates at different levels in the Z direction which provide storage space for assay consumables, samples, standards, controls and containers, thereby increasing the storage capacity for such reagents.

In a preferred embodiment the lowest base plate is firmly fixed to the drawer. At least one upper plate, which is movable in one direction relative to the fixed lowest base plate, is arranged above the latter. The upper plates are preferably smaller than the lowest plate. The uppermost plate is directly accessible by the transporting unit and/or the handing unit. The accessibility of the lower plates is provided by at least one upper plate being movable in at least one direction perpendicular to the Z direction, In an additional preferred embodiment the movement of said upper plate is conducted by at least one protrusion which extends in the Z direction from the holder for the liquid handling probes and is movable in at least one direction perpendicular to the Z direction. In an additional preferred embodiment this protrusion consists of the liquid handling probe that is moved in the X or Y direction and moves the upper plate. In a preferred embodiment removable extensions are attached to said plates which facilitate the movement of the movable plates by the liquid handling probes. The use of such protrusions or liquid handling probes as a means for moving the upper plates of the drawer means that electrical components can be omitted from the drawer, thereby facilitating the design, cleaning and chemical sterilization of the apparatus and reducing the likelihood of detrimental effects due to spilled liquids.

The drawer is extracted or retracted using the protrusions which extend in the Z direction from the holder for the liquid handling probes and are moved in at least one direction and push the drawer or release a hold mechanism. In a preferred embodiment the protrusions consist of the liquid handling probes and they are moved in the Z direction until a predefined position is reached, thereby moving a lever which causes the release of a holding mechanism and the drawer is pushed out by an expanding spring. In this preferred embodiment the spring is compressed by the operator pushing the drawer inwards.

The position of the drawer is checked before the start of the assay procedure by a proximity sensor not attached to the drawer, thus allowing the omission of electrical components from the drawer, In a preferred embodiment the proximity sensor detects the retracted position of the drawer prior to the start of the assay and if this retracted position cannot be verified, the operator is prompted via the user interface to push the drawer to its retracted position.

In a preferred embodiment at least one individual strip of microtitre wells, consisting of a multitude of wells arranged in one direction can be loaded into the drawer by means of a container with cavities for receiving and supporting at least one strip. This container is partly or entirely made of a material with high thermal conductivity, thus ensuring that the thermal equilibrium of the strips with the environment is rapidly achieved. Upon transfer of this container to means for agitation and incubation at predefined temperatures outside the drawer, a frozen strip can be rapidly thawed. Such a system comprising said container and said means for agitation and incubation not present on the drawer adds heating capabilities to the drawer without increasing the complexity of the drawer.

The use of strips instead of complete microtitre plates can have two advantages: Firstly, the use of strips reduces storage space requirements, if not all wells of a microtitre plate are required. Secondly, strips offer a higher flexibility with regard to the ability to combine various reagents than complete microtitre plates.

The strips are located on the container with spacings between the individual strips, thus allowing the detection of at least two machine-readable labels located on different strips present in the container. In a preferred embodiment, the machine-readable labels consist of barcode labels and the container is transported, using the liquid handling probes, to the thermal incubation station for the rapid thawing of the frozen material contained in the strips.

The analyzer of the present invention further comprises a removable dump container, which in a preferred embodiment is located in the drawer for easy access and emptying. The dump container is used for the disposal of used assay consumables such as disposable liquid handling probe tips, and might he also used for microtitre plates and specific assay disposables. The filling level of the dump container is monitored by a sensor not attached to the drawer, thus keeping the drawer free from electrical components. In a preferred embodiment, the sensor consists of an ultrasonic sensor and the filling level of the dump container is checked prior to the start of the assay procedure and if the remaining volume is smaller than the predefined value the operator is prompted via the user interface to empty the dump container.

The presence of the removable dump container is verified by proximity sensors not attached to the drawer. thus keeping the drawer free of electrical components. In a preferred embodiment, the presence of the dump container is checked upon the retraction of the drawer and if no dump container can be detected, the operator is prompted via the user interface to place a dump container in the specified position.

The analyzer further comprises a sensing means for checking the completeness and/or correct positioning of the loaded assay consumables such as the assay reagents, disposable assay consumables, standards, controls and samples in the drawer, and/or for checking the presence or absence of lids, caps or the like. These means are based on the detection of the presence or absence of surfaces. In a preferred embodiment, surfaces are detected by using a gas being pumped by a pump through a nozzle, the nozzle being moved with its opening ahead onto a surface. As soon as the opening comes into contact with the surface the diameter of the opening changes, thus producing changes in the pressure required for pumping the gas through the opening. In a preferred embodiment, the nozzle is part of the liquid handling probe which detects surfaces such as caps, covers, shields, seals and surfaces of pipette tip boxes, microtitre plates, microtitre strips and containers. Alternatively to the issuing of gas through the nozzle the gas can also be aspirated through the nozzle.

An additional means for detecting the presence or absence of surfaces is realized by determining the travel distance not fully travelled by a probe due to its contact with a surface. This is reflected in step losses of the corresponding step actuator driving the probe in Z-direction. Protrusions extending in at least one Z direction and movable in at least one X/Y direction are moved in at least one direction over a predefined distance. If a surface is present in the travel path of the protrusion its movement stops before the predefined position is reached. If a surface is absent, the probe will move the full distance to the predefined position. Differences in the position of a surface will result in differences in the travel distance not covered due to the arrest of the protrusion by the surface. By comparing the detected travel distance with predefined values it is possible to identify the movable containers concerned. The surface contact can be measured also by different means as e.g. electrical impedance, ultrasonic or optical reflection and the like.

In a preferred embodiment the protrusions consist of at least one liquid handling probe that extends in the Z direction from the holder for the liquid handling probes and is lowered in the Z direction at predefined X/Y positions. in this preferred embodiment the liquid handling probe is moved to a predefined position at a reduced speed. In this preferred embodiment the movement of the probe is arrested as soon as it comes into contact with the upper surface of a container present in the drawer and the non-covered distance is quantified by the number of possible steps not performed by the probe actuation motor as soon as the probe returns to its upper endpoint position (the home position). In this preferred embodiment a set of predefined travel distances corresponding to Z positions of target plates is verified accordingly. Target surfaces are consumable containers for assay reagents, assay consumables, standards, controls and samples and specified containers. The incorrect loading of the assay components into the drawer can be identified by this method. Additionally, the presence or absence of caps, lids and the like on assay consumables can be detected by this approach.

In a special embodiment the analyzer of the present invention further contains means for reading machine-readable labels or tags, such as RFID or barcode labels enabling the identification of assay consumables. These means are not attached to the drawer in order to keep the drawer completely free of any electrical components. Information corresponding to the machine-readable labels is stored in a central processing unit. This information can include: type of container, name of reagent, volume of reagent, expiry date, production date, reagent or standard concentration, serial. number, reagent or standard identity, lot or batch number and the like. Corresponding information attached to labels can be used for the identification of assay components in the drawer and the identification of correct loading in terms of position and orientation of the assay components in the drawer. In particular, the attachment of machine-readable labels in a non-symmetrical way to a container enables discrimination between symmetrical translations of the container and the identification of the incorrect rotational positioning of a container such as a microtitre plate, microtitre well strips, sample containers and standard and control containers.

In a preferred embodiment, the container with the assay components loaded into the drawer is transported by the liquid handling probes—using removable extensions attached to the liquid handling probes—to the vicinity of a barcode label reader, where the barcode is read. This allows the identification of the container and a comparison between the attached and the stored information, such as the type of container, the name of the reagent, the volume of the reagent, expiry dates, production dates, the concentrations of the reagents or standards, serial numbers, the identity of the reagents or standards and lots or batch numbers etc. with a predefined set of data. This predefined set of data depends on the predefined and specific assay parameters such as for example sample numbers, assay types, replica numbers, definitions of standards, definitions of controls and dilution factors selected by the operator. In this preferred embodiment with all the predefined parameters in their required range, predefined assays are conducted. If the parameters are not within the required range or a barcode is not readable, the assay is not conducted and the user is informed via the user interface of the error concerned, the reason for the error and easy ways to correct it.

The container filled with liquid can be sealed with sealing means such as film, foil, caps and lids. This sealing means may be pierced and opened by the application of localized pressure on the sealing means. The piercing of the sealing means can be performed by a separate punch station. Piercing is preferably performed by the liquid handling probes. In a preferred embodiment, piercing of the sealing means is achieved by liquid handling probes with specially designed removable tips, and in particular with disposable pipette tips, which are characterized by having a smaller contact area between the sealing means and the tip compared to the liquid dispensing probes.

The analyzer further comprises means for agitating microtitre plates and containers in order to ensure the effective mixing of the liquids. Agitation means are preferably located in the accessible region of the liquid handling probes away from the retractable drawer containing the assay consumables, thus keeping the drawer free from any electrical components. This agitation means includes a support that is movable in at least one direction by actuators, the microtitre plates on the support being moved together with the support. Increased mixing efficiency of at least two different fluids in a microtitre plate is achieved by means of protrusions which are movable in at least one direction and are immersed partly or entirely in the liquid contained in the microtitre plate on the movable support means. The plate is moved in at least one direction perpendicular to the direction of the extension of the protrusions. In a preferred embodiment the protrusions consist of liquid handling probes. In an additional preferred embodiment disposable pipette tips are attached to said liquid handling probes and are immersed in the liquid present on the moved microtitre plate.

The incubation of microtitre plates and containers at predefined temperatures is achieved by means of heated supports, onto which the microtitre plates and containers can be placed. The obtainment of thermal equilibrium between the heated support and the microtitre plate or container is accelerated by the presence of a thermally conductive material between the heated support and the microtitre plates or a container ensuring contact. In a preferred embodiment the heated supports are located within the agitation support.

The detection of optical characteristics such as absorbance, nephelometric or turbidimetric characteristics, luminescence, fluorescence, fluorescence polarization and the time-resolved fluorescence of analytes or analyte-dependent chemical entities is conducted by an optical reading subsystem. In a preferred embodiment this optical reading subsystem is located in a second drawer within the automated analyzer, said drawer being separate from the drawer with the assay components. The drawer with the optical reading subsystem allows occasional access to the optical reading system for maintenance and upgrading purposes and for allowing the precise positioning of the optical reading system once the drawer is retracted. The precise positioning of the optical reading subsystem facilitates interaction between the liquid handling system and the optical reader, in particular when microtitre plates or containers are transported by the liquid handling system to the optical reading subsystem.

The optical subsystem enables the detection of liquid transfer and storage conditions by detecting the optical characteristics of wells and comparing them with predefined optical characteristics relating to the type of assay, the total well volume and the type of microtitre plate, thus allowing the identification of erroneous total well volumes and types of microtitre plates. In a preferred embodiment, the optical parameter consists of the optical measurement height, which is determined by varying the distance between the light-collecting means and the microtitre plate and detecting the height with an extrema or inflection point in the light intensity collected. This height is dependent on the plate characteristics and the liquid volume in the microtitre plate and thus allows the identification of erroneous volumes and types of microtitre plates.

For the detection of analytes, equal incubation times are important, particularly for operations that take place well by well and not over entire plates. The time lapse between each operation depends on the position of the wells on the microtitre plate and can lead to differences in the signals obtained due to differences in the incubation times. In order to avoid these differences in incubation times, each well is given a tag indicating the time of the start of an operational step. The following step for each well is conducted upon the lapse of a predefined period of time in relation to the start of the previous operational step for each well.

Analyte detection reactions resulting in a change in at least one detectable parameter as a function of the incubation time, are analyzed via an endpoint method or a kinetic reading method. The endpoint method is characterized either by a single reading of each reaction well after a specific reaction time according to the specific time tag concerned, or the detection reaction is stopped by adding a stop solution to the reaction wells before the reaction plate is transferred to the microplate reader for reading. The kinetic reading method comprises the repeated detection of the detectable parameter concerned, calculating the first derivative and applying linear regression to at least two data points of the first derivative, thereby reducing errors.

The analyzer also comprises optional means for separating a solid phase from a liquid, which in a preferred embodiment consists of magnetic beads which are separated from the liquid by the application of magnetic fields. Magnetic fields may be applied e.g. by means of a device comprising of a plurality of magnets, the magnets arranged in an array corresponding to the individual wells of a microtitre plate. Alternatively, magnetic probes may be attached to the transporting unit. These probes can lever and release magnetic particles.

The analyzer according to the invention is controlled by a data processor. This can, for example, be a computer with corresponding inputs and outputs for controlling the subsystem, for recording, and storing data and for interacting with a user. Those skilled in the art of automation technology are familiar with data processing devices for programming, controlling and regulating automated processes. Known interfaces such as RS232, USB, CAN bus and the like are preferably used for the communication process, i.e. the exchange of signals between the data processing unit and the subsystem of the analyzer.

The operator interacts with the device via a user interface, which in a preferred embodiment consists of a touch-sensitive liquid crystal display (LCD). The operator can choose between a combination of predefined assay protocols or can himself devise a customized assay protocol. This protocol provides a choice between various assay parameters such as sample numbers, assay types, replica numbers, standards, controls and dilution factors. Depending on the selected assay parameters, the required assay reagents, controls, standards and consumables are determined and the operator is prompted via the user interface to load the specific assay consumables, reagents, controls, standards and samples in predefined and specified positions into the drawer of the apparatus. The drawer is retracted into the device and the correct position, identity, orientation, composition and status of the assay consumables and reagents is verified and machine-readable labels on the sample and assay consumables and reagents are read. If errors in the position, identity, orientation, composition and status of the assay consumables are detected, the operator is informed of the errors, the reason for the errors and easy ways to correct them. If the correct position, identity, orientation, composition and status of the assay consumables is confirmed, the analyzer begins performing tasks such as piercing the container and transporting predefined volumes of the assay reagents, samples, controls and standards onto a microtitre plate. Then, the plate is transported along a predefined path between the integrated subsystems such as agitation, thermal incubation, separation of the solid phase and optical reading, where one or more optical characteristics such as absorbance, luminescence, fluorescence, fluorescence polarization or the time-resolved fluorescence of a well is determined, thus allowing a conclusion to be drawn about the analyte characteristics and stored and displayed together with other predefined values.

The automated analyzer is controlled by software having means to be remotely started by a corresponding network, thus allowing the complete, automated combination of the analyzer and an automated sample delivery system. The software is capable of importing files in common formats such as ASCII and stores results in combination with additional information such as error codes, reagent specifications and optical reader specifications in common formats such as ASCII.

The analyzer is modular; the subsystems can be exchanged easily. Commercially available subsystems can be integrated into the analyzer. As a liquid handling subsystem for example the robotic workstation X100-1-4 available from the company Xiril AG (Hombrechtikon, Switzerland) can be used, which comprises the functionality required to perform the operations described in this document, such as liquid dispensing, uptake and release of pipette tips and extensions, transport of microtitre plates and containers, application of a gas flow and means for pressure detection for the detection of surfaces and so on. As an optical reading subsystem for example Pherastar Plus available from the company BMG Labtech GmbH (Offenburg, Germany) can be used, which comprises the functionality required to perform the operations described in this document, such as the detection of optical characteristics such as absorbance, luminescence, fluorescence, fluorescence polarization and time-resolved fluorescence.

The present invention addresses the need for performing analyte detection without any skilled laboratory personnel and without any auxiliary liquid supply or waste disposal processes. It represents a compact apparatus, which can he operated by personnel with little training, requires only standard electrical connections, anticipates and detects errors, reduces the consequences of spilled liquids and is easy to clean.

The present invention is explained in more detail with the aid of the attached figures which relate to a concrete embodiment without however being limited thereto.

BRIEF DESCRIPTION OF THE SEVERAL VIEWS OF THE DRAWING(S)

DETAILED DESCRIPTION OF THE INVENTION

Figure 1:
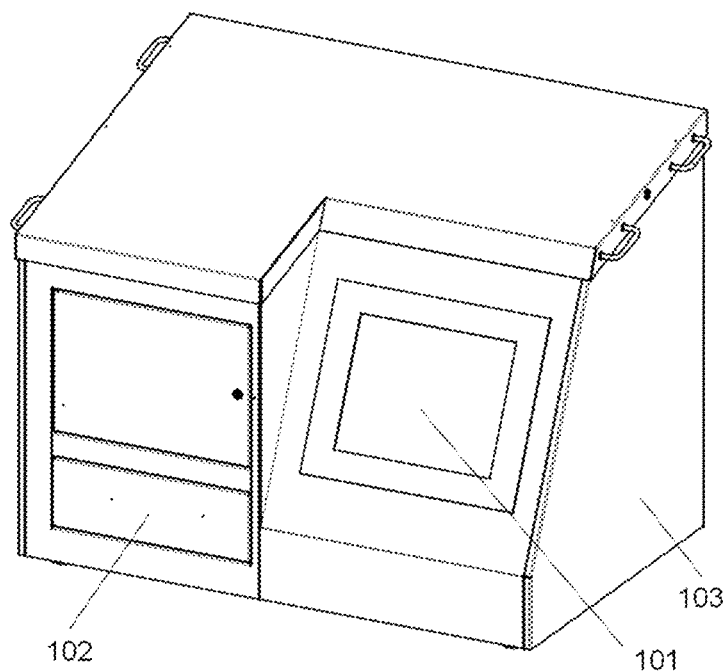
FIG. 1 shows a perspective front view of one embodiment of the analyzer.

FIG. 1 shows a perspective front view of one embodiment of the analyzer according to the invention. The device is operated via a touch-sensitive display (101). A drawer (102) provides the user with physical access to the device. The device is otherwise shielded from external effects by a housing (103).

Figure 2:
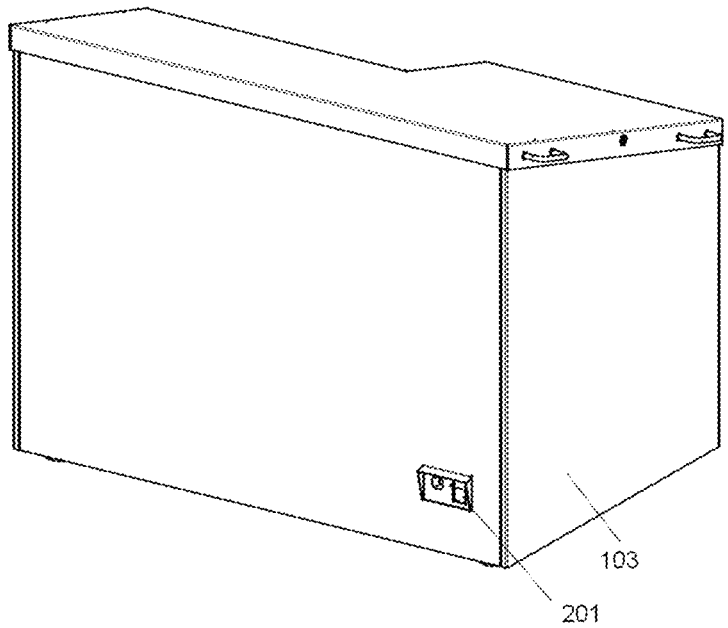
FIG. 2 shows a perspective view of the rear side of an analyzer.

FIG. 2 shows a perspective view of the rear side of an analyzer, on which the main switch (201) for switching the device on and off is located.

Figure 3:
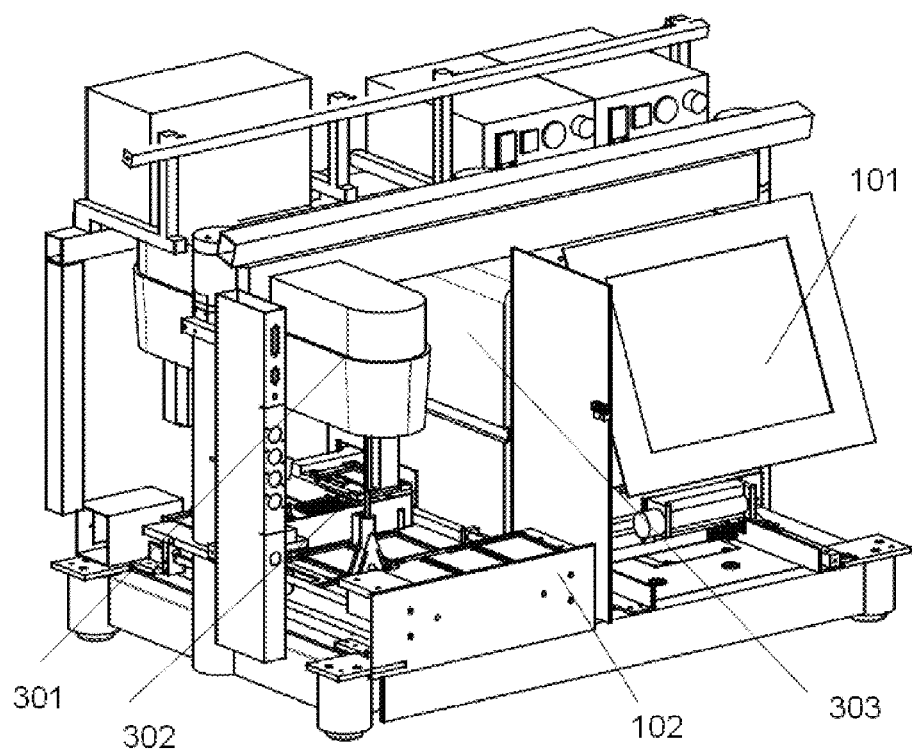
FIG. 3 shows a perspective front view of the analyzer without its housing.

FIG. 3 shows a perspective front view of the analyzer without its housing. The touch-sensitive display (101) is used for operating the device. The drawer (102) can be opened for supplying the device with samples and reagents. The transporting unit comprises a holder (301) which can be moved in two directions (X and Y) which are vertical to the force of gravity and to each other. Liquid handling probes (302), which can also he moved vertically to the X,Y plane (in the Z direction), are attached to the holder. The device has an optical reading subsystem (303) for the detection of optical characteristics such as absorbance, luminescence, fluorescence, fluorescence polarization and time-resolved fluorescence.

Figure 4:
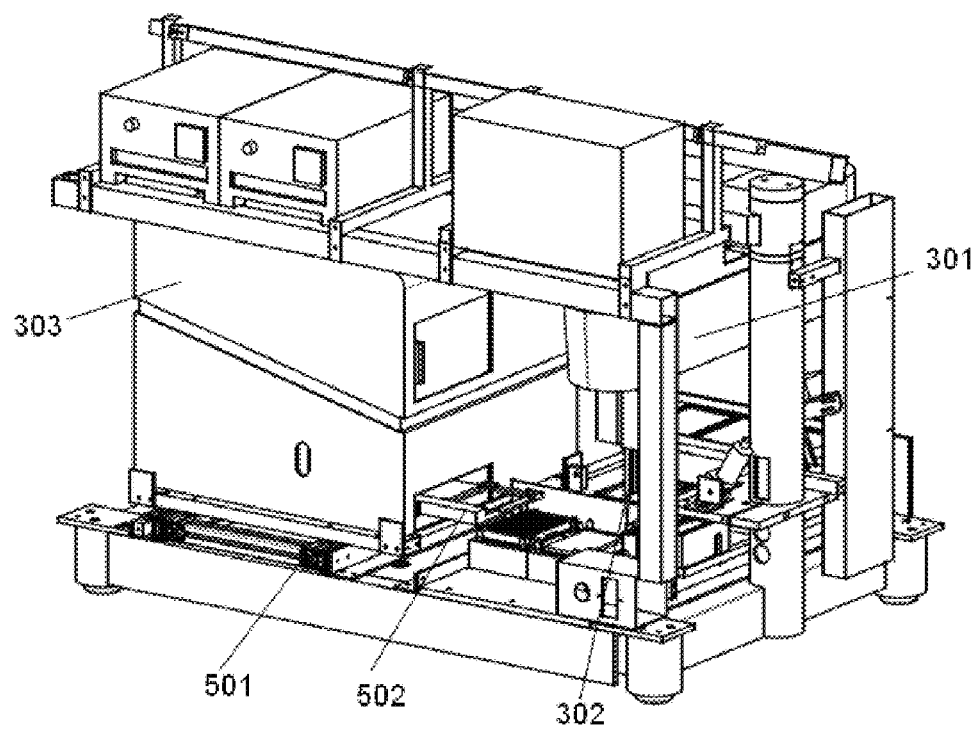
FIG. 4 shows a rear perspective view of the analyzer without its housing.

FIG. 4 shows a rear perspective view of the analyzer without its housing. In addition to the elements already depicted in FIG. 3, FIG. 4 also shows a drawer (502) in the optical reading subsystem, into which the microtitre plates can be transported for optical analysis via the transporting unit. The optical reading subsystem is preferably contained in a drawer (501) to allow it to be removed from the analyzer for servicing or other purposes (see also FIG. 14).

Figure 5:
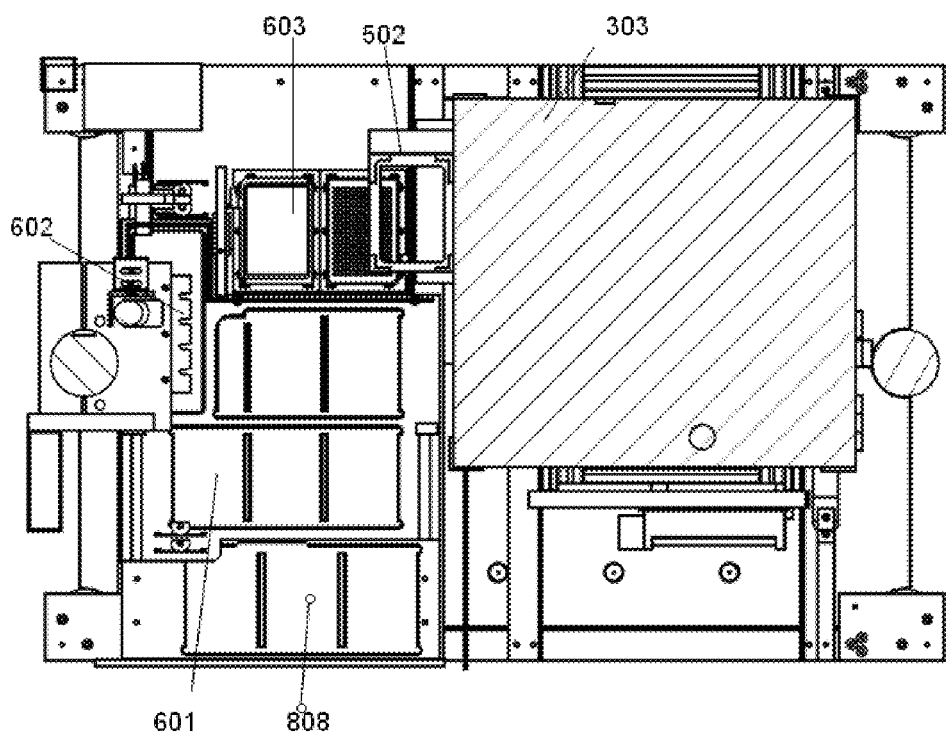
FIG. 5 shows a top view of an analyzer according to the invention without its housing.

FIG. 5 shows a top view of an analyzer according to the invention without its housing. The drawer contains a base and upper plate (601, 808) for holding microtitre plates, assay reagents and containers. Outside the drawer a device for removing pipette tips (602) as well as agitation and incubation stations (603) are located.

Figure 6:
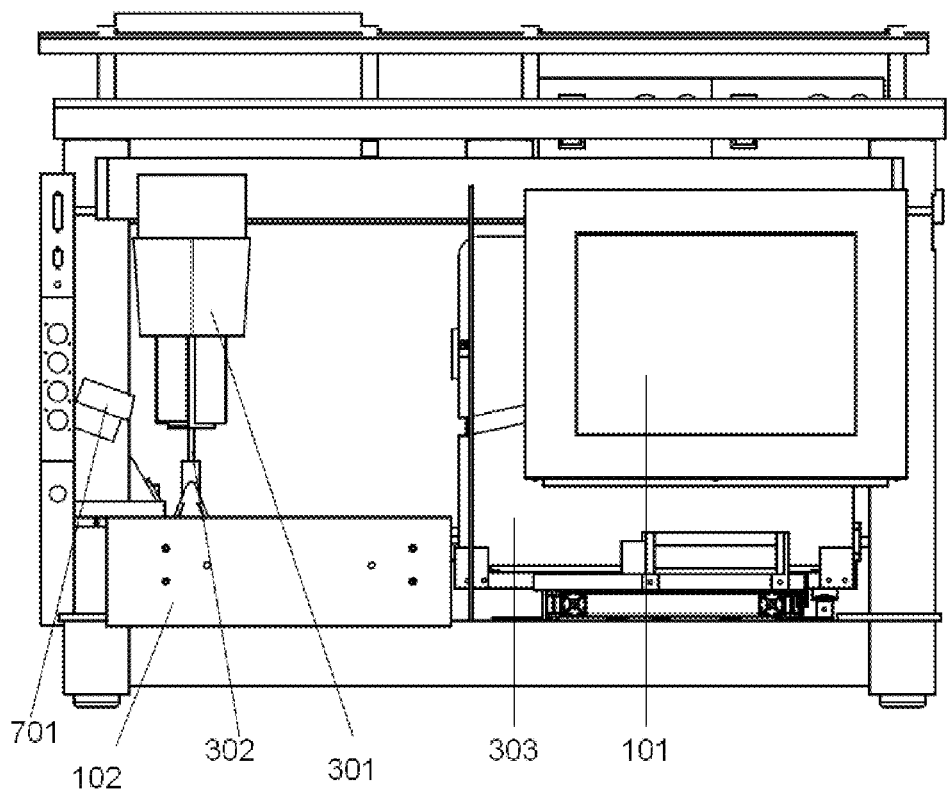
FIG. 6 shows a front view of an analyzer according to the invention without the housing.

FIG. 6 shows a front view of an analyzer according to the invention without the housing. In addition to the elements already shown in the above figures, FIG. 6 also shows a reading device (701), with which identification labels on the microtitre plates can be read. In the present case this is a barcode reader for reading barcodes attached e.g. to the microtitre plates.

Figure 7:
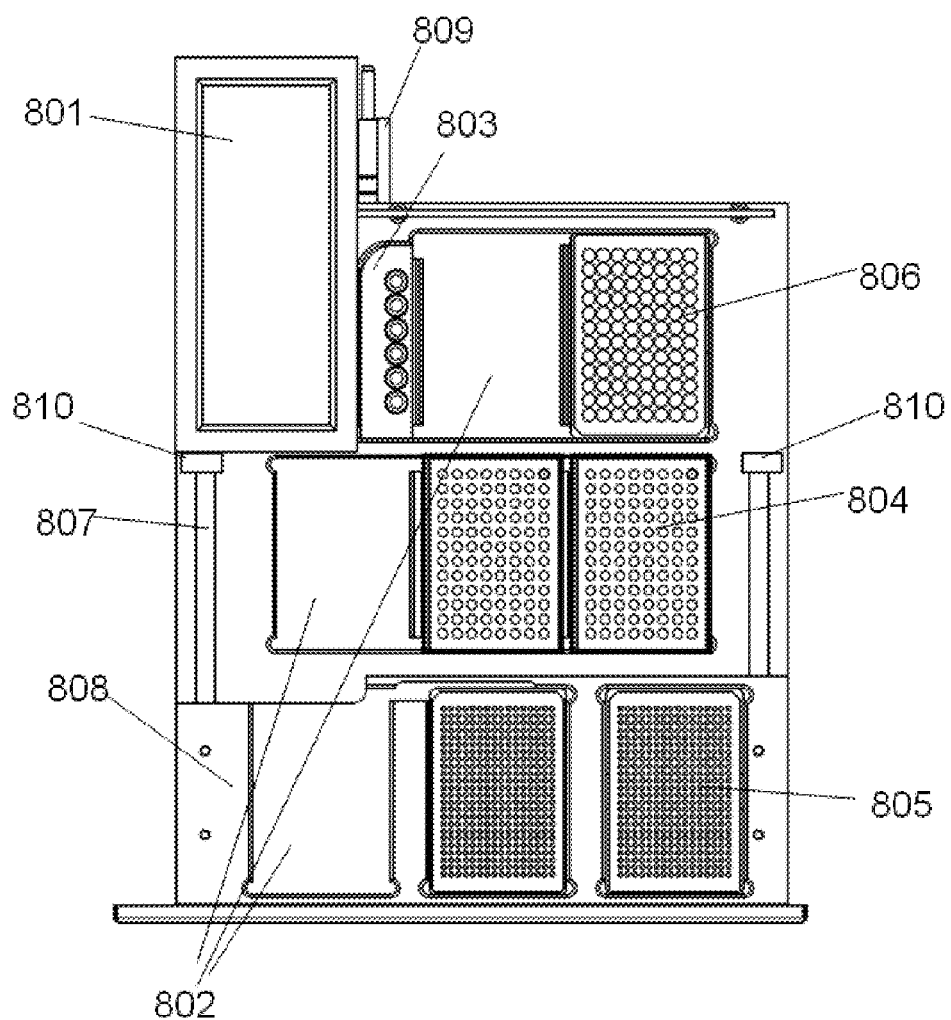
FIG. 7 shows a drawer according to the invention for supplying the analyzer with samples and reagents from above.

FIG. 7 shows a drawer according to the invention for supplying the analyzer with samples and reagents from above. it includes an upper plate (808) which can be moved in the same direction as the bottom plate firmly attached to the drawer. The upper plate is smaller than the lower plate. Guiding rods (807) allow the upper plate to be moved until it reaches holding-down means (810). A dump container (801) is arranged on the drawer for receiving waste. Wells are present for receiving microtitre plates (802) and containers (803) for receiving samples to be analyzed. In the example of FIG. 7 the drawer contains two 384-well (805) microtitre plates in its front region and one 96-well (806) micro-titre plates in its middle region. The base plate also contains two boxes with 96 pipette tips (804).

Figure 8:
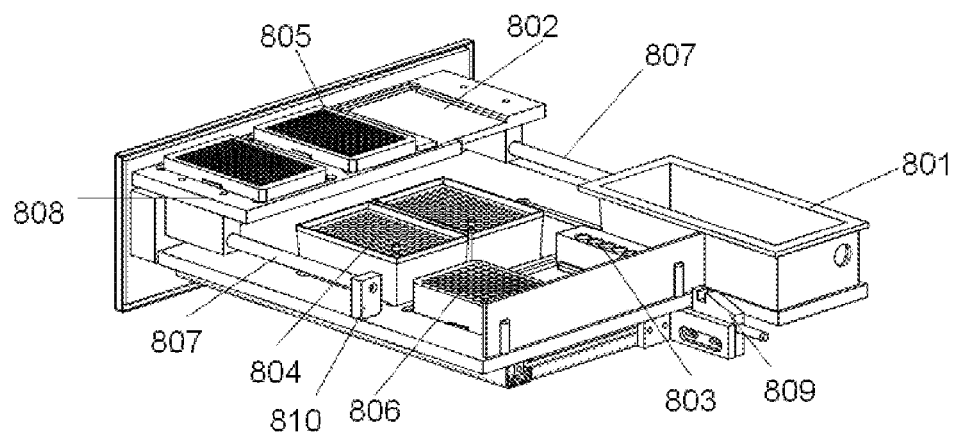
FIG. 8 shows a rear perspective view of a drawer according to the invention.

FIG. 8 shows a rear perspective view of a drawer according to the invention. In addition to the elements already shown in FIG. 7, FIG. 8 shows a wedge-shaped arresting device (809) with a recess which is used for fixing the drawer within the analyzer.

Figure 9:
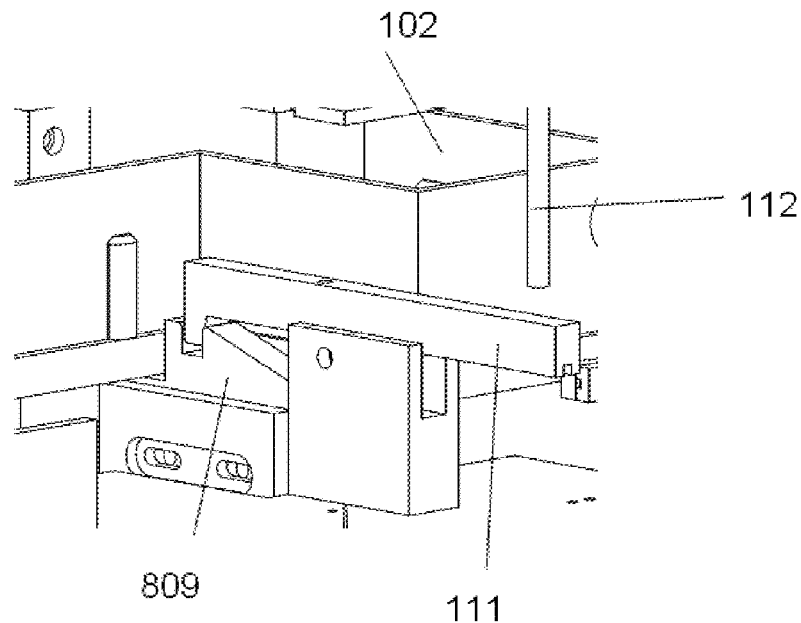
FIG. 9 shows an enlarged view of the arresting device from FIG. 8.

FIG. 9 shows an enlarged view of the arresting device (809) from FIG. 8. In addition, a lever (111) is shown which is attached to the analyzer outside the drawer and which can engage in the recess in the arresting device (809) by means of a protrusion. A movable protrusion (112) can also be seen which can lift the protrusion on the lever (111) out of the recess in the arresting device (see also FIG. 10). The movably designed protrusion (112) is preferably a liquid handling probe.

Figure 10:
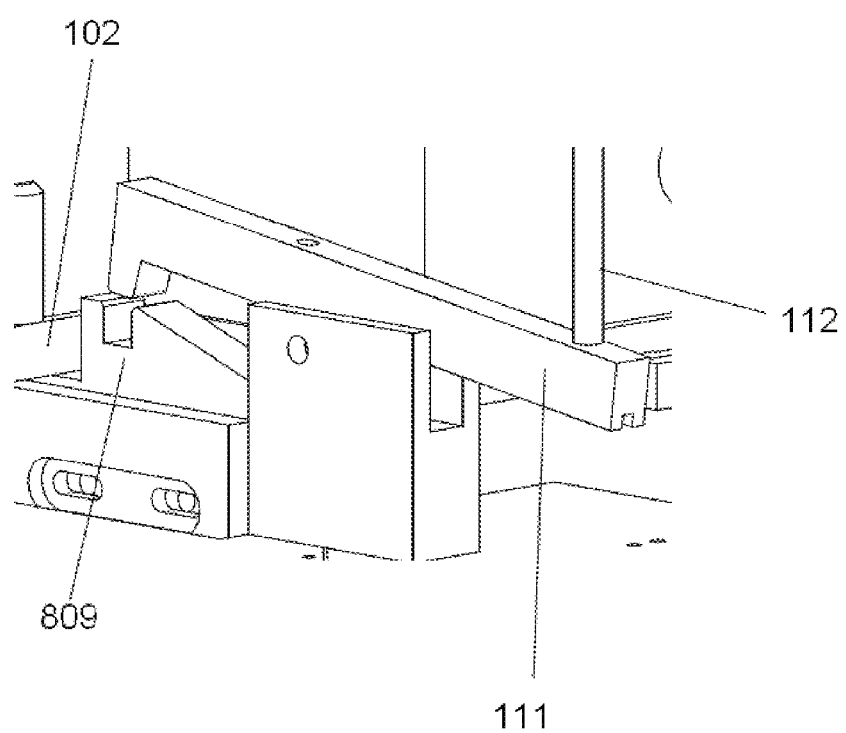
FIG. 10 shows the same section as FIG. 9, except that the movable protrusion has released the lever from its anchorage in the arresting device.

FIG. 10 shows the same section as FIG. 9, except that the movable protrusion (112) has released the lever from its anchorage in the arresting device. The movably designed protrusion (112) is preferably a liquid handling probe.

Figure 11:
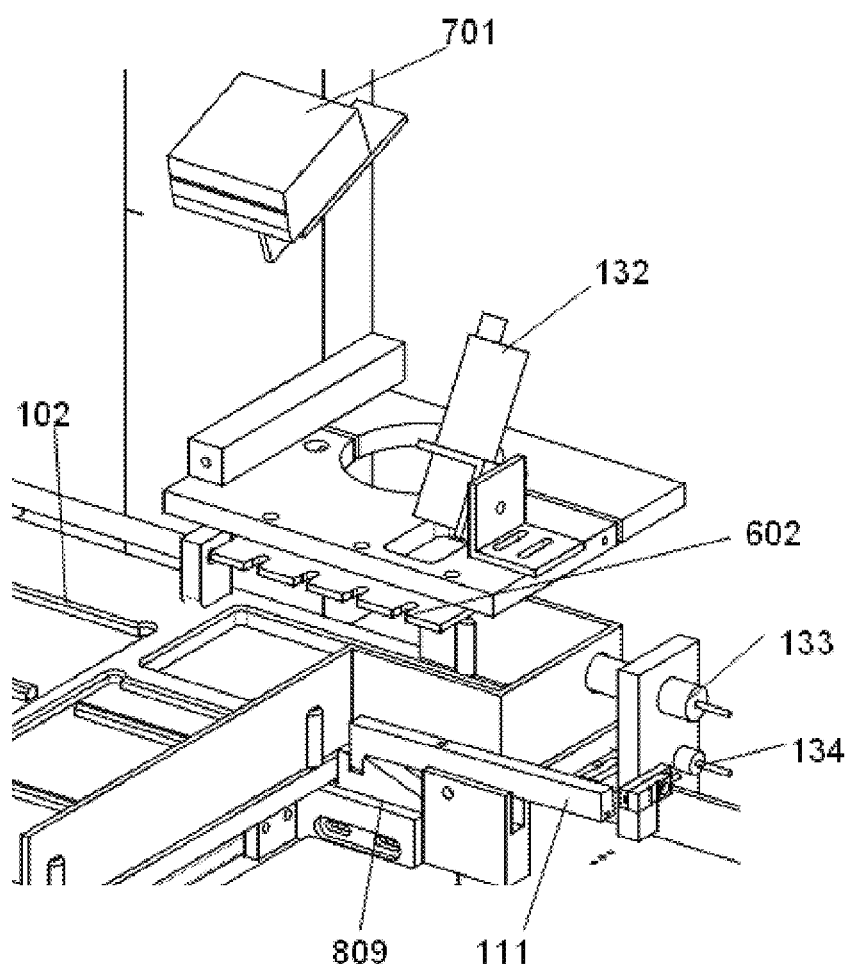
FIG. 11 shows an enlarged section of the analyzer according to the invention in addition to the elements already shown in the preceding figures.

FIG. 11 shows an enlarged section of the analyzer according to the invention in addition to the elements already shown in the preceding figures. FIG. 11 also shows a slanting barcode reading device (701), With the aid of an ultrasonic sensor (132) the level of filling of the waste container can be checked. Proximity sensors (133, 134) detect the presence of the drawer of the insertion/removal system and the removable extensions.

Figure 12:
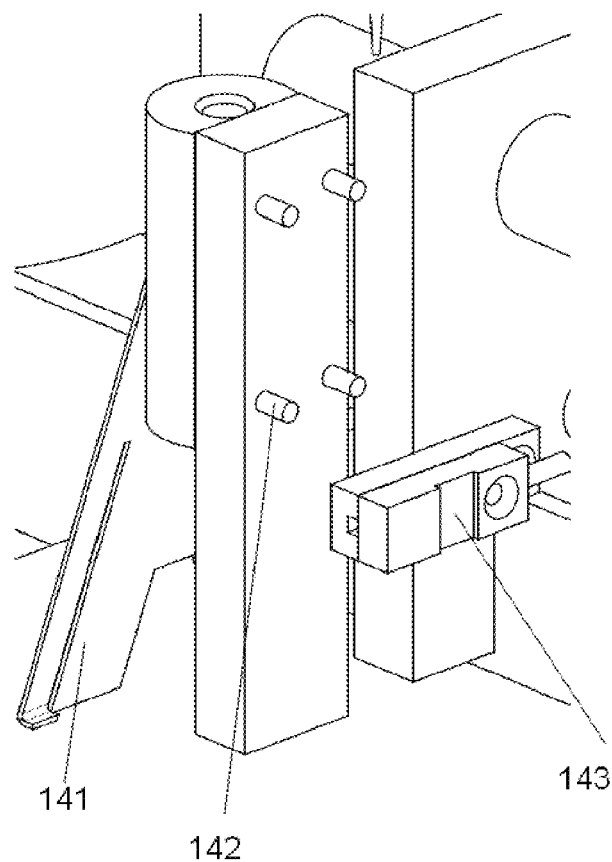
FIG. 12 shows an enlarged section of the analyzer according to the invention.

FIG. 12 shows an enlarged section of the analyzer according to the invention. In addition to the elements already shown in the preceding figures, FIG. 12 also shows a removable extension (141) which is positioned separately from the movable protrusions and has horizontal protrusions (142) which are used for maintaining and overcoming the adhesive forces between the liquid handling probes and the removable extensions. In addition, a sensor element in the form of a proximity sensor (143) is shown.

Figure 13:
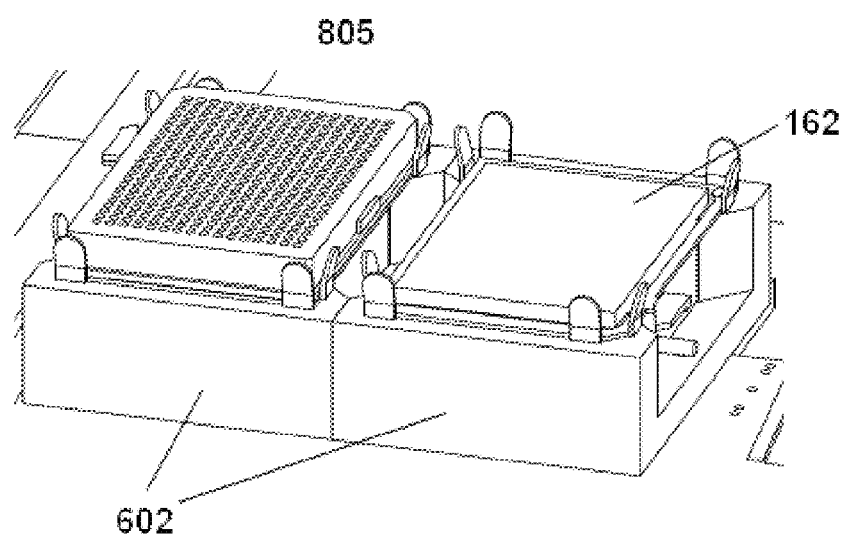
FIG. 13 shows an enlarged section of the analyzer according to the invention.

FIG. 13 shows an enlarged section of the analyzer according to the invention. This is an agitation and incubation means (602) which is fitted with supports (162). A microtitre plate is located on the support on the left. The topography of the supports is adapted to the dimensions of the microtitre plates e.g. a plane surface for a microtitre plates with plane well bottoms or a plate with conically shaped cavities for accepting conically shaped wells from e.g. a low-volume 384 microtitre plate.

Figure 14:
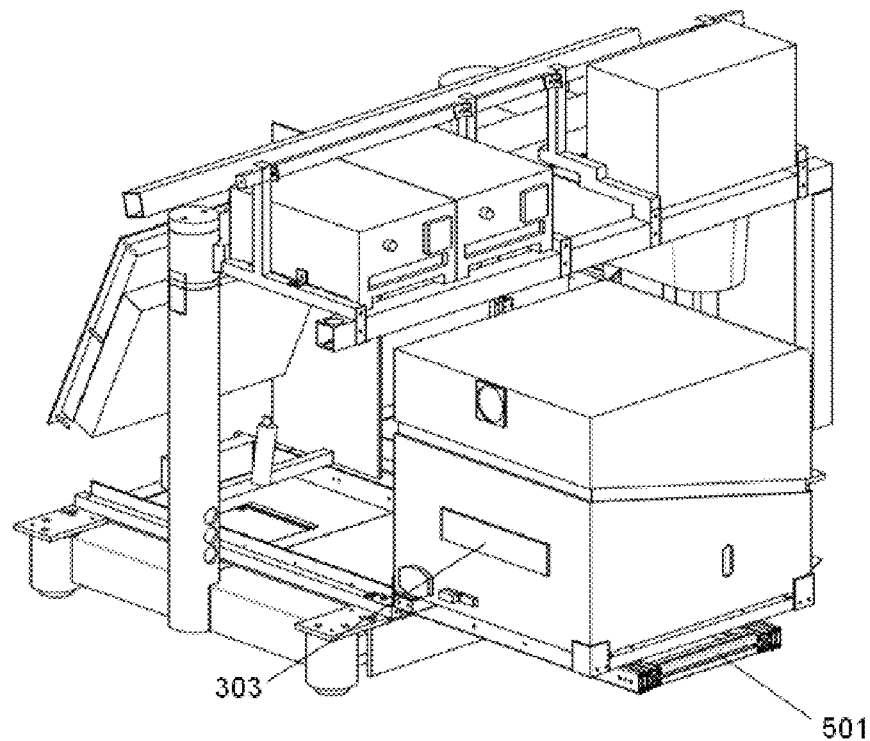
FIG. 14 shows a preferred embodiment of the analyzer.

FIG. 14 shows a preferred embodiment of the analyzer according to the invention, in which the optical reading subsystem can be removed from the analyzer for servicing and other purposes via guide bars (501).

Figure 15:
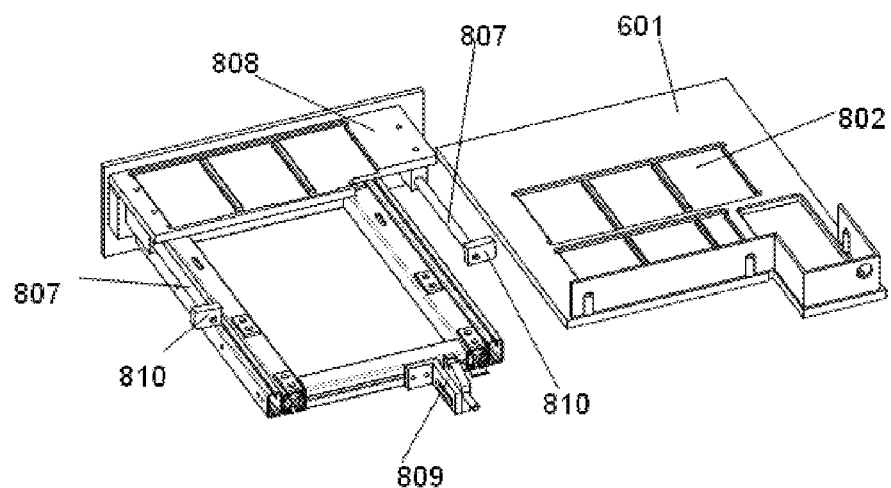
FIG. 15 shows a top perspective view of a drawer according to the invention

FIG. 15 shows a top perspective view of a drawer according to the invention in which the base plate (601) has been removed. The drawer and the base plate are designed in such a manner that they can be connected to each other and detached from each other without the use of tools, so that an operator can easily exchange the base plate.

Figure 16:
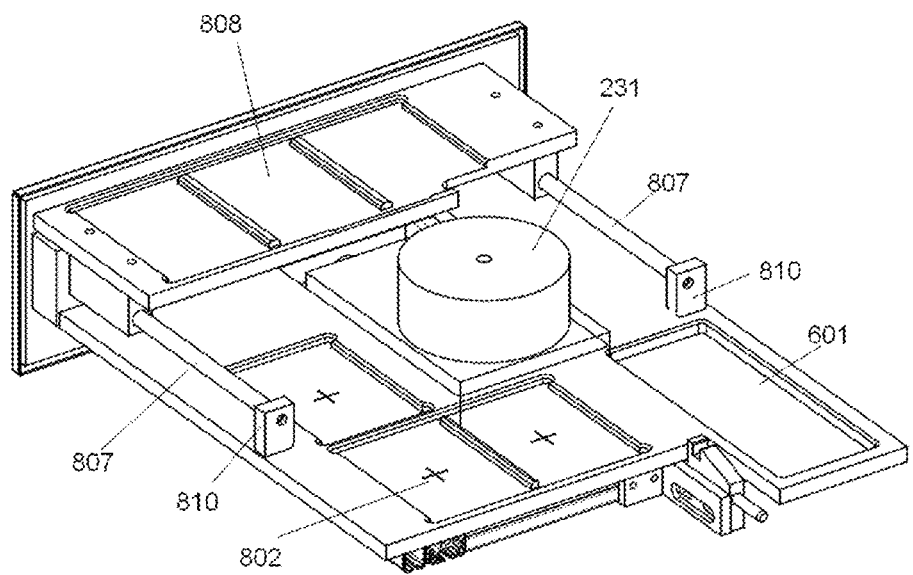
FIG. 16 shows a perspective view of a drawer according to the invention.

FIG. 16 shows a perspective view of a drawer according to the invention for supplying the analyzer with samples and reagents. In this figure the base plate of FIG. 7 has been exchanged for a base plate containing elements for gravimetric determination (231).

Figure 17:
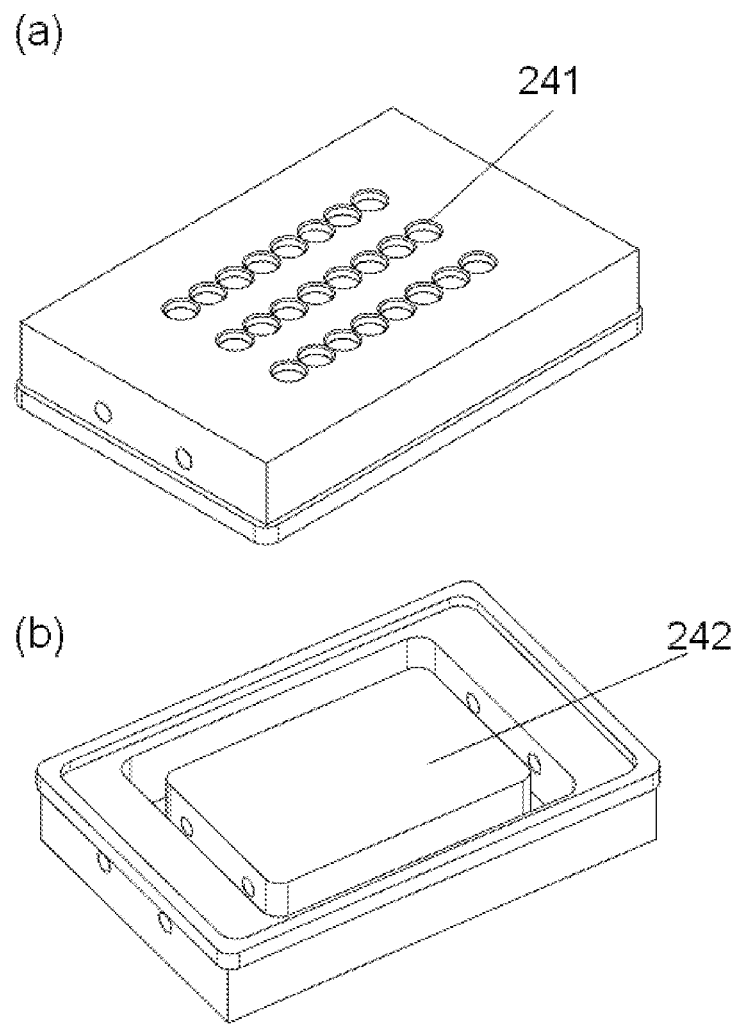
FIG. 17 shows a top (a) and a bottom (b) view of a container for strips.

FIG. 17 shows a top (a) and a bottom (b) view of a container for strips. The container has cavities (241), into which strips can be introduced. The bottom section of the figure shows the underneath side of a preferred embodiment of a container for strips, in which the cavities for receiving the strips are contained in a carrier made of a material (242) with high thermal conductivity which allows rapid thermal equilibration.

Figure 18:
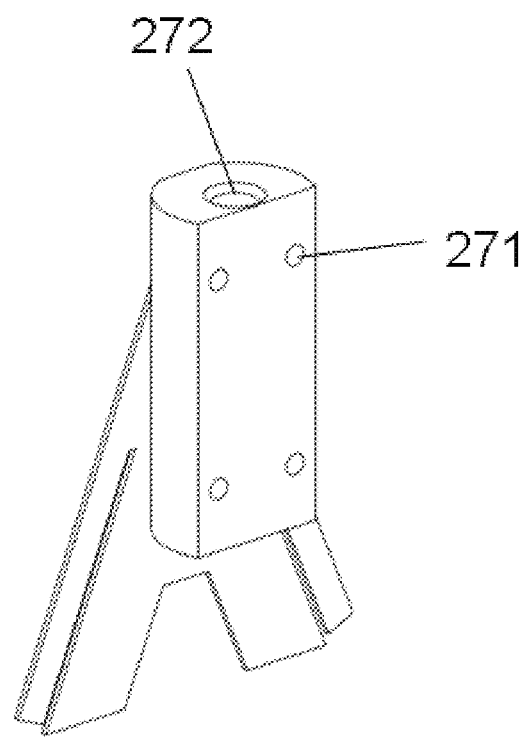
FIG. 18 shows a preferred embodiment of a removable extension with a conical cavity (272) in the Z direction.

FIG. 18 shows a preferred embodiment of a removable extension with a conical cavity (272) in the Z direction which can form adhesive contact with the movable protrusions. The movably designed protrusion is preferably a liquid handling probe. in addition, the removable extension has cavities (271) in a direction vertical to the Z direction, into which protrusions of holders for the removable extensions fit, in order to be able to pull the removable extensions away from the movable protrusions.

REFERENCE NUMERALS 101 touch-sensitive display
102 drawer
103 housing
111 lever with a protrusion for arresting the drawer in the analyzer
112 movably designed protrusion
132 ultrasonic sensor
133 proximity sensor
134 proximity sensor
141 removable extension
142 horizontal protrusions
143 proximity sensor
162 support
201 main switch
231 weighing device for gravimetric determination
241 cavity
242 support made of a thermally conductive material
271 cavities in a direction vertical to the Z direction
272 conical cavity in the Z direction
301 movable arm of the pipetting device
302 liquid handling probe
303 optical reading subsystem
501 drawer for containing the optical reading subsystem
502 drawer of the optical reading subsystem
601 base plate
602 device for removing pipette tips
603 agitation and incubation station
701 barcode reading device
801 dump container
802 wells for receiving microtitre plates
803 container for receiving samples to be analyzed
804 disposable pipette tip holder
805 microtitre plate
806 microtiter plate
807 guide bars
808 upper plate
809 arresting device for the drawer
810 holding-down means

The invention claimed is:
1. An apparatus for automatically performing chemical, biochemical, or biological analyses in microtiter plates which comprises:
    a housing containing
    a plurality of subsystems for performing different operations on microtiter plates;
    a transporting subsystem for automated movement of microtiter plates in three directions X, Y, and Z in order to transport plates from one subsystem to another subsystem within the apparatus;
    a liquid handler comprising at least two liquid handling probes, wherein said liquid handler is integrated in the transporting subsystem; and an insertion/removal subsystem for inserting, removing, and storing microtiter plates and equipment for sampling and dilution operations wherein said insertion/removal subsystem comprises at least one drawer and is mechanically operated, without the need for electrical components implemented in that subsystem; wherein the at least one drawer is pushed into an analyzer and engages a spring element in said housing, the drawer being fixed in the analyzer by an arresting device which is released by the transporting subsystem.

2. The apparatus according to claim 1, wherein the insertion/removal subsystem comprises at least one drawer which is opened and/or closed by the transporting subsystem.

3. The apparatus according claim 2, wherein the at least one drawer comprises at least one replaceable base plate which has wells for receiving microtiter plates and reagents.

4. The apparatus according to claim 2, wherein at least one drawer comprises at least lower and upper plates, the lower plate being firmly connected to the drawer, whereas the upper plate is smaller than the lower plate and is designed to be movable in at least one direction relative to the lower plate and can be moved by a protrusion on the transporting unit.

5. The apparatus according to claim 1, wherein the transportation of microtiter plates is carried out by removable extensions which are reversibly connected to the liquid handling probes.

6. The apparatus according to claim 1, further comprising a container made of material with high thermal conductivity for receiving strips, wherein strips are arranged in the container in such a manner that a slanting barcode reader can read all of the barcodes each attached to one side of each strip.

7. The apparatus according to claim 1, wherein the subsystem for optical reading is mounted on an additional drawer.

8. The apparatus according to claim 1, further comprising a RFID reader to read out RFID tags attached to assay consumables.

9. The apparatus according claim 1, further comprising an analyzer element checker to check the presence or absence or the correct positioning of elements within an analyzer.

10. The apparatus according to claim 9, wherein the checking is carried out by recording pressure changes which occur when a nozzle from which gas issues or into which gas is aspirated approaches a surface which changes a flow cross-section of the nozzle.

11. The apparatus according to claim 9, wherein the checking is carried out by comparing a distance actually travelled by a protrusion on the transporting unit with a predefined travel distance.

12. The apparatus according to claim 1, wherein sensors are used which detect the presence of a dump container, the drawer and/or the removable extensions and/or the filling level of the dump container.

13. The apparatus according to claim 1, further comprising a liquid dispenser checker to check the correct dispensing of liquids, wherein optical characteristics in wells are detected and compared with predefined characteristics.

14. A method of automatically conducting chemical, biochemical, or biological analyses comprising the steps of
   providing a housing;
   providing a plurality of subsystems each performing different operations on microtiter plates;
   providing a transporting subsystem for the automated movement of microtiter plates in three directions X, Y, and Z in order to transport plates from one subsystem to another within the apparatus;
   providing a liquid handler comprising at least two liquid handling probes, wherein said liquid handler is integrated in the transporting subsystem;
   providing an insertion/removal subsystem for inserting, removing, and storing microtiter plates and equipment for sampling an dilution operations, wherein said insertion/removal subsystem comprises at least one drawer and is mechanically operated, without the need for electrical components implemented in that subsystem; wherein the at least one drawer is pushed into an analyzer and engages a spring element in said housing, the drawer being fixed in the analyzer by an arresting device which is released by the transporting subsystem.

15. The method according to claim 14, wherein, after a liquid has been introduced into a container, a liquid handling probe with a disposable tip attached remains in the container for a predefined time, during which the container is agitated.

16. The method according to claim 14, wherein sequential operations are conducted on individual wells of the microtiter plates and the points in time of the operations concerned are recorded in order to ensure an identical period of time between two operations for all of the wells.

17. The apparatus according to claim 1, wherein the different operations are selected from the group consisting of agitation, thermal incubation and optical reading for the detection of optical characteristics.

18. The apparatus according to claim 17, wherein the optical characteristics are selected from the group consisting of absorbance, luminescence, fluorescence, fluorescence polarization and time-resolved fluorescence.

19. The method according to claim 14, wherein the different operations are selected from the group consisting of agitation, thermal incubation and optical reading for the detection of optical characteristics.

20. The method according to claim 19, wherein the optical characteristics are selected from the group consisting of absorbance, luminescence, fluorescence, fluorescence polarization and time-resolved fluorescence.

* * * * *